US009775625B2

(12) United States Patent
Schoenefeld

(10) Patent No.: US 9,775,625 B2
(45) Date of Patent: Oct. 3, 2017

(54) PATIENT-MATCHED SURGICAL COMPONENT AND METHODS OF USE

(71) Applicant: Biomet Manufacturing, LLC, Warsaw, IN (US)

(72) Inventor: Ryan J. Schoenefeld, Fort Wayne, IN (US)

(73) Assignee: Biomet Manufacturing, LLC., Warsaw, IN (US)

(*) Notice: Subject to any disclaimer, the term of this patent is extended or adjusted under 35 U.S.C. 154(b) by 5 days.

(21) Appl. No.: 14/694,389

(22) Filed: Apr. 23, 2015

(65) Prior Publication Data

US 2015/0327947 A1 Nov. 19, 2015
US 2017/0224417 A9 Aug. 10, 2017

Related U.S. Application Data

(63) Continuation of application No. 12/142,142, filed on Jun. 19, 2008, now abandoned.
(Continued)

(51) Int. Cl.
*A61B 34/00* (2016.01)
*A61B 17/15* (2006.01)
(Continued)

(52) U.S. Cl.
CPC .......... *A61B 17/15* (2013.01); *A61B 17/1703* (2013.01); *A61B 34/10* (2016.02);
(Continued)

(58) Field of Classification Search
CPC ........................ A61B 34/20; A61B 2034/2055
(Continued)

(56) References Cited

U.S. PATENT DOCUMENTS

| | | |
|---|---|---|
| 5,016,639 A | 5/1991 | Allen |
| 5,094,241 A | 3/1992 | Allen |
| 5,097,839 A | 3/1992 | Allen |
| 5,119,817 A | 6/1992 | Allen |
| 5,142,930 A | 9/1992 | Allen et al. |
| 5,222,499 A | 6/1993 | Allen et al. |
| 5,230,338 A | 7/1993 | Allen et al. |
| 5,389,101 A | 2/1995 | Heilbrun et al. |
| 5,397,329 A | 3/1995 | Allen |
| 5,603,318 A | 2/1997 | Heilbrun et al. |
| 5,682,886 A | 11/1997 | Delp et al. |
| 5,682,890 A | 11/1997 | Kormos et al. |

(Continued)

FOREIGN PATENT DOCUMENTS

| | | |
|---|---|---|
| EP | 0427358 A1 | 5/1991 |
| EP | 0649117 A2 | 4/1995 |

(Continued)

OTHER PUBLICATIONS

"Advanced Science for Real Living™", PMI® Patient-Matched Implants, [Online]. Retrieved from the Internet: http://www.biomet.com/hcp/pmi, (May 31, 2007).

(Continued)

*Primary Examiner* — Anu Ramana
(74) *Attorney, Agent, or Firm* — Schwegman Lundberg & Woessner, P.A.

(57) ABSTRACT

A patient matched surgical component including a body having a surface that is preoperatively shaped to substantially mate with the shape of an anatomical feature of a patient in a predefined spatial relationship, the surface being shaped by preoperatively identifying a finite number of bony anatomical landmarks on a representative model of the anatomical feature, and a reference array preoperatively integrated with a surgical navigation tracking system in a predefined spatial orientation relative to the anatomical feature, the reference array being couplable to the body such that when the surgical component is installed onto the anatomical feature intraoperatively, the position of the anatomical feature relative to the reference array is automatically recognized by the surgical navigation system.

24 Claims, 11 Drawing Sheets

Related U.S. Application Data

(60) Provisional application No. 60/944,817, filed on Jun. 19, 2007.

(51) Int. Cl.
 *A61B 17/17* (2006.01)
 *A61B 90/00* (2016.01)
 *A61B 34/10* (2016.01)
 *A61B 34/20* (2016.01)

(52) U.S. Cl.
 CPC .............. *A61B 34/20* (2016.02); *A61B 90/36* (2016.02); *A61B 90/37* (2016.02); *A61B 2034/102* (2016.02); *A61B 2034/105* (2016.02); *A61B 2034/108* (2016.02); *A61B 2034/2055* (2016.02); *A61B 2090/3983* (2016.02)

(58) Field of Classification Search
 USPC ....................................................... 606/86 R
 See application file for complete search history.

(56) References Cited

U.S. PATENT DOCUMENTS

| | | | |
|---|---|---|---|
| 5,772,594 | A | 6/1998 | Barrick |
| 5,836,954 | A | 11/1998 | Heilbrun et al. |
| 5,871,018 | A | 2/1999 | Delp et al. |
| 5,902,239 | A | 5/1999 | Buurman |
| 6,069,932 | A | 5/2000 | Peshkin et al. |
| 6,167,145 | A | 12/2000 | Foley et al. |
| 6,198,794 | B1 | 3/2001 | Peshkin et al. |
| 6,205,411 | B1 | 3/2001 | Digioia, III et al. |
| 6,235,038 | B1 | 5/2001 | Hunter et al. |
| 6,381,485 | B1 | 4/2002 | Hunter et al. |
| 6,402,762 | B2 | 6/2002 | Hunter et al. |
| 6,428,547 | B1 | 8/2002 | Vilsmeier et al. |
| 6,434,415 | B1 | 8/2002 | Foley et al. |
| 6,470,207 | B1 | 10/2002 | Simon et al. |
| 6,553,152 | B1 | 4/2003 | Miller et al. |
| 6,584,174 | B2 | 6/2003 | Schubert et al. |
| 6,674,916 | B1 | 1/2004 | Deman et al. |
| 6,724,922 | B1 | 4/2004 | Vilsmeier |
| 6,754,374 | B1 | 6/2004 | Miller et al. |
| 6,772,002 | B2 | 8/2004 | Schmidt et al. |
| 6,776,526 | B2 | 8/2004 | Zeiss |
| 6,782,287 | B2 | 8/2004 | Grzeszczuk et al. |
| 6,856,826 | B2 | 2/2005 | Seeley et al. |
| 6,856,827 | B2 | 2/2005 | Seeley et al. |
| 6,892,088 | B2 | 5/2005 | Faulkner et al. |
| 6,895,268 | B1 | 5/2005 | Rahn et al. |
| 6,926,673 | B2 | 8/2005 | Roberts et al. |
| 6,947,582 | B1 | 9/2005 | Vilsmeier et al. |
| 6,978,166 | B2 | 12/2005 | Foley et al. |
| 6,990,220 | B2 | 1/2006 | Ellis et al. |
| 7,010,095 | B2 | 3/2006 | Mitschke et al. |
| 7,525,309 | B2 | 4/2009 | Sherman et al. |
| 7,618,451 | B2 * | 11/2009 | Berez ................ A61B 5/1076 606/84 |
| 8,421,642 | B1 * | 4/2013 | McIntosh ................ G06F 3/017 340/539.1 |
| 2001/0007918 | A1 | 7/2001 | Vilsmeier et al. |
| 2001/0011175 | A1 | 8/2001 | Hunter et al. |
| 2002/0183610 | A1 | 12/2002 | Foley et al. |
| 2003/0059097 | A1 | 3/2003 | Abovitz et al. |
| 2004/0030245 | A1 | 2/2004 | Noble et al. |
| 2004/0087852 | A1 | 5/2004 | Chen et al. |
| 2004/0127788 | A1 | 7/2004 | Arata |
| 2005/0015003 | A1 | 1/2005 | Lachner et al. |
| 2005/0015022 | A1 | 1/2005 | Richard et al. |
| 2005/0015099 | A1 | 1/2005 | Momoi et al. |
| 2005/0020911 | A1 | 1/2005 | Viswanathan et al. |
| 2005/0021043 | A1 | 1/2005 | Jansen et al. |
| 2005/0021044 | A1 | 1/2005 | Stone et al. |
| 2005/0033117 | A1 | 2/2005 | Ozaki et al. |
| 2005/0033149 | A1 | 2/2005 | Strommer et al. |
| 2005/0038337 | A1 | 2/2005 | Edwards |
| 2005/0049477 | A1 | 3/2005 | Fu et al. |
| 2005/0049478 | A1 | 3/2005 | Kuduvalli et al. |
| 2005/0049486 | A1 | 3/2005 | Urquhart et al. |
| 2005/0054915 | A1 | 3/2005 | Sukovic et al. |
| 2005/0054916 | A1 | 3/2005 | Mostafavi |
| 2005/0059873 | A1 | 3/2005 | Glozman et al. |
| 2005/0085714 | A1 | 4/2005 | Foley et al. |
| 2005/0085715 | A1 | 4/2005 | Dukesherer et al. |
| 2005/0085717 | A1 | 4/2005 | Shahidi |
| 2005/0085718 | A1 | 4/2005 | Shahidi |
| 2005/0085720 | A1 | 4/2005 | Jascob et al. |
| 2005/0090730 | A1 | 4/2005 | Cortinovis et al. |
| 2005/0090733 | A1 | 4/2005 | Van Der Lugt et al. |
| 2005/0096515 | A1 | 5/2005 | Geng |
| 2005/0096535 | A1 | 5/2005 | De La Barrera |
| 2005/0101970 | A1 | 5/2005 | Rosenberg |
| 2005/0113960 | A1 | 5/2005 | Karau et al. |
| 2005/0119561 | A1 | 6/2005 | Kienzle, III |
| 2005/0119565 | A1 | 6/2005 | Pescatore |
| 2005/0119639 | A1 | 6/2005 | Mccombs et al. |
| 2005/0124988 | A1 | 6/2005 | Terrill-grisoni et al. |
| 2005/0137599 | A1 | 6/2005 | Masini |
| 2005/0148850 | A1 | 7/2005 | Lahm et al. |
| 2005/0148855 | A1 | 7/2005 | Kienzle, III |
| 2005/0197568 | A1 | 9/2005 | Vass et al. |
| 2005/0197569 | A1 | 9/2005 | Mccombs |
| 2005/0203373 | A1 | 9/2005 | Boese et al. |
| 2005/0203374 | A1 | 9/2005 | Vilsmeier |
| 2005/0203375 | A1 | 9/2005 | Willis et al. |
| 2005/0203383 | A1 | 9/2005 | Moctezuma de la Barrera et al. |
| 2005/0203384 | A1 | 9/2005 | Sati et al. |
| 2005/0215879 | A1 | 9/2005 | Chuanggui |
| 2005/0216032 | A1 | 9/2005 | Hayden |
| 2005/0228250 | A1 | 10/2005 | Bitter et al. |
| 2005/0228270 | A1 | 10/2005 | Lloyd et al. |
| 2005/0228404 | A1 | 10/2005 | Vandevelde et al. |
| 2005/0234335 | A1 | 10/2005 | Simon et al. |
| 2005/0251026 | A1 | 11/2005 | Stone |
| 2005/0251030 | A1 | 11/2005 | Azar et al. |
| 2005/0277832 | A1 | 12/2005 | Foley et al. |
| 2005/0288575 | A1 | 12/2005 | De La Barrera et al. |
| 2005/0288578 | A1 | 12/2005 | Durlak |
| 2006/0004284 | A1 | 1/2006 | Grunschlager et al. |
| 2006/0009780 | A1 | 1/2006 | Foley et al. |
| 2006/0015030 | A1 | 1/2006 | Poulin et al. |
| 2006/0025677 | A1 | 2/2006 | Verard et al. |
| 2006/0036149 | A1 | 2/2006 | Lavigna et al. |
| 2006/0036151 | A1 | 2/2006 | Ferre et al. |
| 2006/0036162 | A1 | 2/2006 | Shahidi et al. |
| 2006/0058604 | A1 | 3/2006 | Avinash et al. |
| 2006/0058615 | A1 | 3/2006 | Mahajan et al. |
| 2006/0058616 | A1 | 3/2006 | Marquart et al. |
| 2006/0058644 | A1 | 3/2006 | Hoppe et al. |
| 2008/0269596 | A1 | 10/2008 | Revie et al. |

FOREIGN PATENT DOCUMENTS

| | | |
|---|---|---|
| EP | 1226788 A1 | 7/2002 |
| GB | 2246936 A | 2/1992 |
| WO | WO-02062248 A1 | 8/2002 |
| WO | WO-2004001569 A2 | 12/2003 |
| WO | WO-2004006770 A2 | 1/2004 |
| WO | WO-2004069036 A2 | 8/2004 |

OTHER PUBLICATIONS

"Advanced Science for Real Living™", Evolution of a Patient-Matched Implant, [Online]. Retrieved from the Internet: http://www.biomet.com/hcp/pmi/evolution.cfm, (May 31, 2007).

"Advanced Science for Real Living™", Design and Manufacture, [Online]. Retrieved from the Internet: http://www.biomet.com/hcp/pmi/design.cfm, (May 31, 2007).

"Advanced Science for Real Living™", CT Scan Protocol, [Online]. Retrieved from the Internet: http://www.biomet.com/hcp/pmi/ctscan.cfm, (May 31, 2007).

(56) References Cited

OTHER PUBLICATIONS

"Advanced Science for Real Living™", Image Gallery PMI® Patient-Matched Implants, [Online]. Retrieved from the Internet: http://www.biomet.com/hcp/pmi/images.cfm, (May 31, 2007).
"Advanced Science for Real Living™", Acetabulum/Pelvis for Oncology, [Online]. Retrieved from the Internet: http://www.biomet.com/hcp/pmi/acetscan.cfm, (May 31, 2007).
"Advanced Science for Real Living™", Patient-Matched Implants, [Online]. Retrieved from the Internet:http://www.biomet.com/hcp/pmi/samples.cfm, (May 31, 2007).
"U.S. Appl. No. 12/142,142, Final Office Action mailed Aug. 30, 2012", 6 pgs.
"U.S. Appl. No. 12/142,142, Final Office Action mailed Oct. 31, 2014", 7 pgs.
"U.S. Appl. No. 12/142,142, Non Final Office Action mailed Jan. 20, 2012", 7 pgs.
"U.S. Appl. No. 12/142,142, Non Final Office Action mailed May 9, 2014", 6 pgs.
"U.S. Appl. No. 12/142,142, Response filed Apr. 18, 2012 to Non Final Office Action mailed Jan. 20, 2012", 12 pgs.
"U.S. Appl. No. 12/142,142, Response filed Aug. 6, 2014 to Non Final Office Action mailed May 9, 2014", 13 pgs.
"U.S. Appl. No. 12/142,142, Response filed Sep. 27, 2012 to Final Office Action mailed Aug. 30, 2012", 12 pgs.
"U.S. Appl. No. 12/142,142, Response filed Nov. 7, 2011 to Restriction Requirement mailed Oct. 11, 2011", 8 pgs.
"U.S. Appl. No. 12/142,142, Restriction Requirement mailed Oct. 11, 2011", 5 pgs.

* cited by examiner

PATIENT-MATCHED SURGICAL COMPONENT AND METHODS OF USE

RELATED APPLICATIONS

This application is a continuation of U.S. patent application Ser. No. 12/142,142 filed Jun. 19, 2008, which in turn claims the benefit of U.S. Provisional Patent Application Ser. No. 60/944,817, filed Jun. 19, 2007, the complete disclosures of which are hereby expressly incorporated in their entireties herein by this reference.

FIELD OF THE INVENTION

The present teachings relate generally to surgical navigation, and more particularly to patient-matched surgical components that are adapted to conform to a patient's anatomy, as well as to methods for using such surgical components during a surgical navigation procedure.

BACKGROUND

Surgical navigation systems, also known as computer assisted surgery systems and image guided surgery systems, aid surgeons in locating patient anatomical structures, guiding surgical instruments, and implanting medical devices with a high degree of accuracy. Surgical navigation has been compared to a global positioning system that aids vehicle operators to navigate the earth. A surgical navigation system typically includes a computer, a tracking system, and patient anatomical information. The patient anatomical information can be obtained by using an imaging mode such as fluoroscopy, magnetic resonance imaging (MRI), computer tomography (CT) or by simply defining the location of patient anatomy with the surgical navigation system. Surgical navigation systems can be used for a wide variety of surgeries to improve patient outcomes.

To successfully implant a medical device, surgical navigation systems often employ various forms of computing technology, as well as utilize intelligent instruments, digital touch devices, and advanced 3-D visualization software programs. All of these components enable surgeons to perform a wide variety of standard and minimally invasive surgical procedures and techniques. Moreover, these systems allow surgeons to more accurately plan, track and navigate the placement of instruments and implants relative to a patient's body, as well as conduct preoperative and intra-operative body imaging.

To accomplish the accurate planning, tracking and navigation of surgical instruments, tools and/or medical devices during a surgical procedure utilizing surgical navigation, surgeons often couple "tracking arrays" to the surgical components. These tracking arrays allow the surgeons to track the physical location of these surgical components, as well as the patient's bones during the surgery. By knowing the physical location of the tracking array, software associated with the tracking system can accurately calculate the position of the tracked component relative to a surgical plan image.

It is known to use surgical navigation instruments to measure the size and general contour of a bone before selecting and/or manufacturing a prosthetic implant. This process allows the surgeon to choose a prosthetic component that generally resembles the shape and size of the patient's anatomy, thereby achieving a more customized fit during the implantation process. Despite such customization efforts, most orthopaedic procedures still require the use of adjustable components or guides during the surgical procedure, particularly as such instruments are needed to fit the prosthetic components to the patient's anatomy. However, this process is time consuming, as well as subject to error during the placement and registration of the surgical components. As such, it would be desirable to improve this process to reduce surgery time and improve prosthetic fit and/or function.

SUMMARY OF THE INVENTION

The present teachings provide a patient matched surgical component that is custom manufactured to fit a patient's anatomy in a precise manner. To achieve such customization, the patient's anatomy is preoperatively scanned and uploaded to a software program, which then recreates a three-dimensional model of the patient's anatomy from the scanned image. The three-dimensional model is then used by the software program to identify and locate on the image specific known anatomical landmarks of the patient's anatomy. Planning software then analyzes the identified anatomical landmarks together with any specific surgical instructions needed to develop and plan a surgical protocol for the patient. Once the surgical protocol has been approved by the surgeon, the protocol is presented to a software program, which then uses the protocol, as well as the preoperative scan images, to create a virtual patient matched surgical component. The virtual component is then sent to a rapid prototyping machine or a standard machining process, which in turn manufactures the surgical component for use during the surgical procedure. Because the surgical component is custom manufactured to fit the patient's anatomy relative to specific anatomical landmarks, it can be manufactured with a reference array positioned on its surface in a predefined spatial relationship with respect to the patient's anatomy. By having a predefined spatial relationship between the reference array and the patient's anatomy, the need for intra-operative registration during the surgical procedure is minimized or even eliminated altogether. Furthermore, since the patient matched component is fixable to the patient's anatomy with pins, the reference array can act as an automatically registered rigid bone reference marker that can be used throughout the surgical navigation procedure.

According to one aspect of the present teachings, a method of automatically registering a surgical navigation system to a patient's anatomy is provided. The method comprises programming a surgical navigation system with a first spatial relationship between a surgical component and a reference array connected to the surgical component, programming the surgical navigation system with a second spatial relationship between an anatomical feature of a patient and the surgical component, installing the surgical component on the patient such that the surgical component engages the anatomical feature in the second spatial relationship, and locating the reference array with the surgical navigation system. The navigation system automatically recognizes the position of the reference array relative to the patient's anatomy.

According to another exemplary embodiment herein, a method of performing a surgical procedure aided by a surgical navigation system is provided. The method comprises generating a representative model of an anatomical feature from an image of a patient's anatomy, using the model to make a surgical component, installing the surgical component on the anatomical feature by mating the surface of the component with the anatomical feature in the predefined spatial relationship, and tracking movement of the anatomical feature with a tracking system when the installed surgical component is moved within a measurement field of the tracking system. According to this embodiment, the surgical component has a surface that is shaped to substantially mate with the anatomical feature in a predefined spatial relationship.

According to yet another exemplary embodiment herein, a patient matched surgical component is provided. The surgical component comprises a body having a surface that is shaped to substantially mate with the shape of an anatomical feature of a patient in a predefined spatial relationship, and a reference array connected to the body, the reference array being trackable by a tracking system when exposed to a measurement field of the tracking system.

In still another exemplary embodiment, a method of performing a surgical procedure aided by a surgical navigation system is provided. According to this exemplary embodiment, the method comprises generating a representative model of an anatomical feature from an image of a patient's anatomy, using the model to make a surgical component, the surgical component having a reference array associated therewith and a surface that is shaped to substantially mate with an anatomical feature in a predefined spatial relationship, installing the surgical component on the anatomical feature by mating the surface of the component with the anatomical feature in the predefined spatial relationship, tracking movement of the anatomical feature with the tracking system when the installed surgical component is moved within a measurement field of the tracking system, removing a portion of the anatomical feature, the removed portion also including a portion of the installed surgical component, and tracking a remaining portion of the anatomical feature with the tracking system, the remaining portion of the anatomical feature including a portion of the installed surgical component, the remaining portion of the installed surgical component including the reference array.

BRIEF DESCRIPTION OF THE DRAWINGS

The above-mentioned aspects of the present teachings and the manner of obtaining them will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION

The embodiments of the present teachings described below are not intended to be exhaustive or to limit the invention to the precise forms disclosed in the following detailed description. Rather, the embodiments are chosen and described so that others skilled in the art may appreciate and understand the principles and practices of the present teachings.

Figure 1:
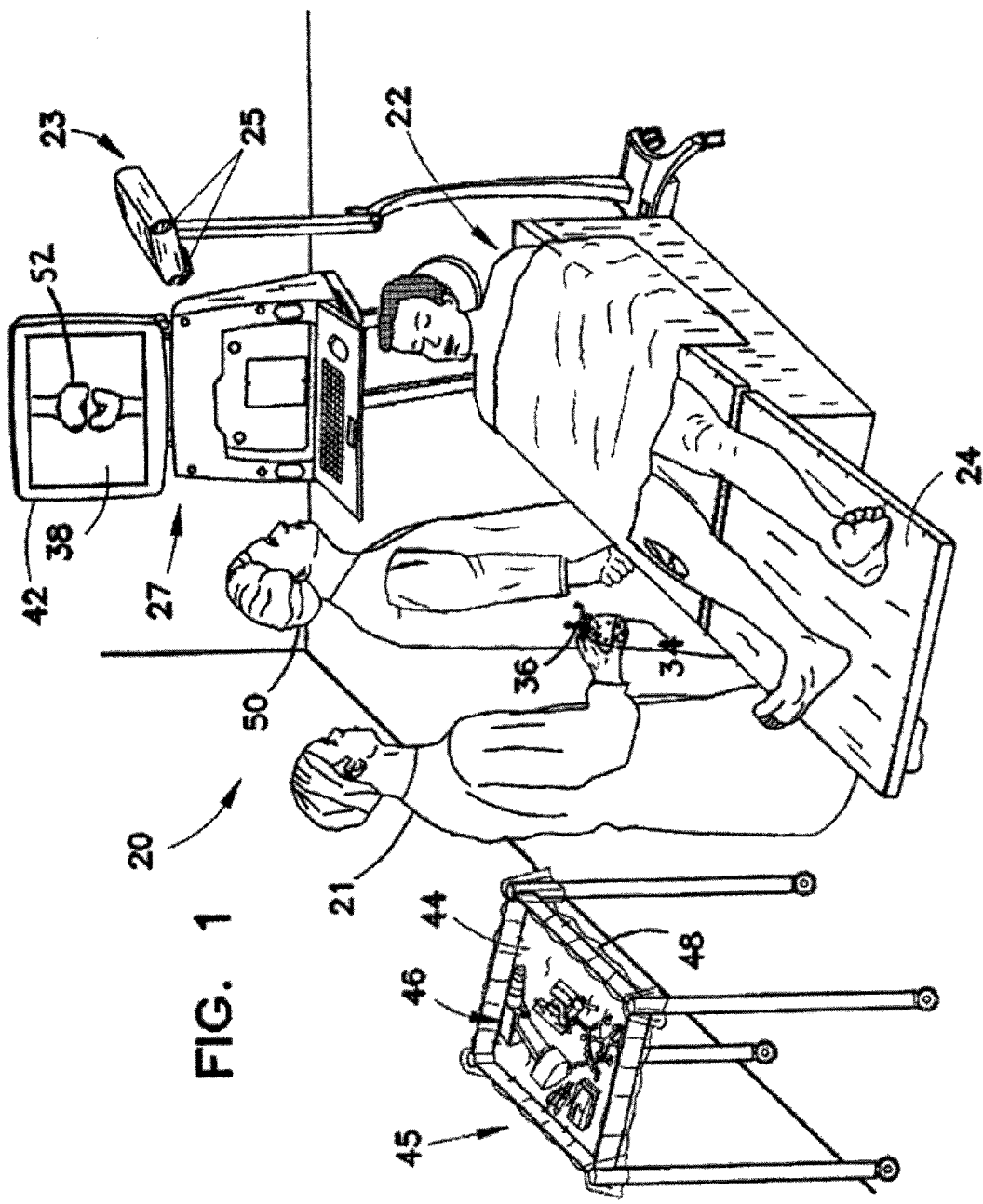
FIG. 1 is a perspective view of an exemplary operating room setup in a surgical navigation embodiment in accordance with the present teachings.

FIG. 1 shows a perspective view of an operating room with surgical navigation system 20. Surgeon 21 is aided by surgical navigation system 20 in performing knee arthroplasty, also known as knee replacement surgery, on patient 22 shown lying on operating table 24. Surgical navigation system 20 has a tracking system that locates arrays and tracks them in real-time. To accomplish this, the surgical navigation system includes optical locator 23, which has two CCD (charge couple device) cameras 25 that detect the positions of the arrays in space by using triangulation methods. The relative location of the tracked arrays, including the patient's anatomy, can then be shown on a computer display (such as computer display 27 for instance) to assist the surgeon during the surgical procedure. The arrays that are typically used include probe arrays, instrument arrays, reference arrays, and calibrator arrays. The tracking system also detects the location of reference array 36, which is attached to patient matched surgical component 34. The relative location of patient matched surgical component 34 with respect to the patient's anatomy can then be shown on computer display image 38 of computer monitor 42. The operating room also includes instrument cart 45 having tray 44 for holding a variety of surgical instruments and arrays 46. Instrument cart 45 is also draped in sterile cover 48 to eliminate contamination risks within the sterile field.

The surgery is performed within a sterile field, adhering to the principles of asepsis by all scrubbed persons in the operating room. Patient 22, surgeon 21 and assisting clinician 50 are prepared for the sterile field through appropriate scrubbing and clothing. The sterile field will typically extend from operating table 24 upward in the operating room. Typically, the computer display is located outside of the sterile field.

A representation of the patient's anatomy 52 can be acquired with an imaging system, a virtual image, a morphed image, or a combination of imaging techniques. The imaging system can be any system capable of producing images that represent the patient's anatomy such as a fluoroscope producing x-ray two-dimensional images, computer tomography (CT) producing a three-dimensional image, magnetic resonance imaging (MRI) producing a three-dimensional image, ultrasound imaging producing a two-dimensional image, and the like. A virtual image of the patient's anatomy can be created by defining anatomical points with the surgical navigation system 20 or by applying a statistical anatomical model. A morphed image of the patient's anatomy can be created by combining an image of the patient's anatomy with a data set, such as a virtual image of the patient's anatomy.

The tracking system of the present invention can be any system that can determine the three-dimensional location of devices carrying or incorporating markers that serve as tracking indicia. More particularly, the tracking system may be an active tracking system that has a collection of infrared light emitting diode (ILEDs) illuminators surrounding the position sensor lenses to flood a measurement field of view with infrared light. Alternatively, the system may be a passive tracking system, which incorporates retro-reflective markers that reflect infrared light back to the position sensor, and the system triangulates the real-time position (x, y, and z location) and orientation (rotation around x, y, and z axes). In yet other embodiments, the tracking system may be a hybrid tracking system that detects active and active wireless markers in addition to passive markers. Active marker based instruments enable automatic tool identification, program control of visible LEDs, and input via tool buttons. Finally, in yet other exemplary embodiments, the tracking system may utilize electromagnetic tracking techniques. These systems locate and track devices and produce a real-time, three-dimensional video display of the surgical procedure by using electromagnetic field transmitters that generate a local magnetic field around the patient's anatomy.

The present teachings enhance surgical navigation system 20 by incorporating into the system a process for custom manufacturing patient-matched surgical component 34 so that it fits the anatomy of patient 22 in a precise manner. Particularly, in addition to tracking surgical components, the navigation system can also generate preoperative images of the patient's anatomy and then use such images to manufacture a surgical component that is custom matched to the patient's anatomy. More specifically, the patient's anatomy is preoperatively scanned and uploaded to a software program, which then recreates a three-dimensional virtual model of the patient's anatomy from the scanned image. The virtual model is then used by the software program to identify and locate known bony anatomical landmarks or predefined points of the patient's anatomy. For a further description about the acquisition and registration of bony landmarks, see U.S. patent application Ser. No. 11/689,711, entitled "Modeling Method and Apparatus for use in Surgical Navigation," filed Mar. 22, 2007, which is incorporated by reference herein in its entirety.

As is appreciated by those of skill within the art, bony anatomical landmarks are visible points or locations on a patient's anatomy, which are identifiable by referencing known locations on the surface of the bone. For instance, known bony landmarks on the femur include, but are not limited to, a femoral head landmark, a central knee landmark, a medial femoral condyle landmark, a lateral femoral condyle landmark, a medial epicondyle landmark, a lateral epicondyle landmark, a medial posterior condyle landmark, a lateral posterior condyle landmark and an anterior cortex point landmark. Similar bony landmarks are also found on other bones (such as the tibia, fibula, patella and pelvis, for instance), however, for simplicity purposes, the exemplary illustrations provided here are specifically directed to the femur. As the present teachings are not intended to be limiting, it should be understood and appreciated that these teachings are also applicable to bony landmark structures other than the femur.

Planning software analyzes the identified anatomical landmarks together with any specific surgical instructions received from the surgeon and develops a surgical procedure or protocol for the patient. After its approval, the protocol is then entered into a software program, which uses the protocol together with the preoperative scan images to create a virtual representation of a patient matched surgical component. The virtual representation of the surgical component is then sent to a rapid prototyping machine or a standard machining process, which in turn manufactures a physical prototype of the surgical component. Because the surgical component is custom manufactured to fit the patient's anatomy relative to known anatomical landmarks, it can be manufactured to include a reference array that extends from its surface in a predefined manner. By having the reference array positioned in a predefined spatial orientation with respect to the patient's anatomy, the need to further register the component intraoperatively is unnecessary; particularly as the registration of the reference array is completed preoperatively during the surgical planning stages. Furthermore, since the patient matched component can be secured to the patient's anatomy, the reference array can also function as an automatically registered and trackable bone reference array during the surgical procedure.

Figure 2:
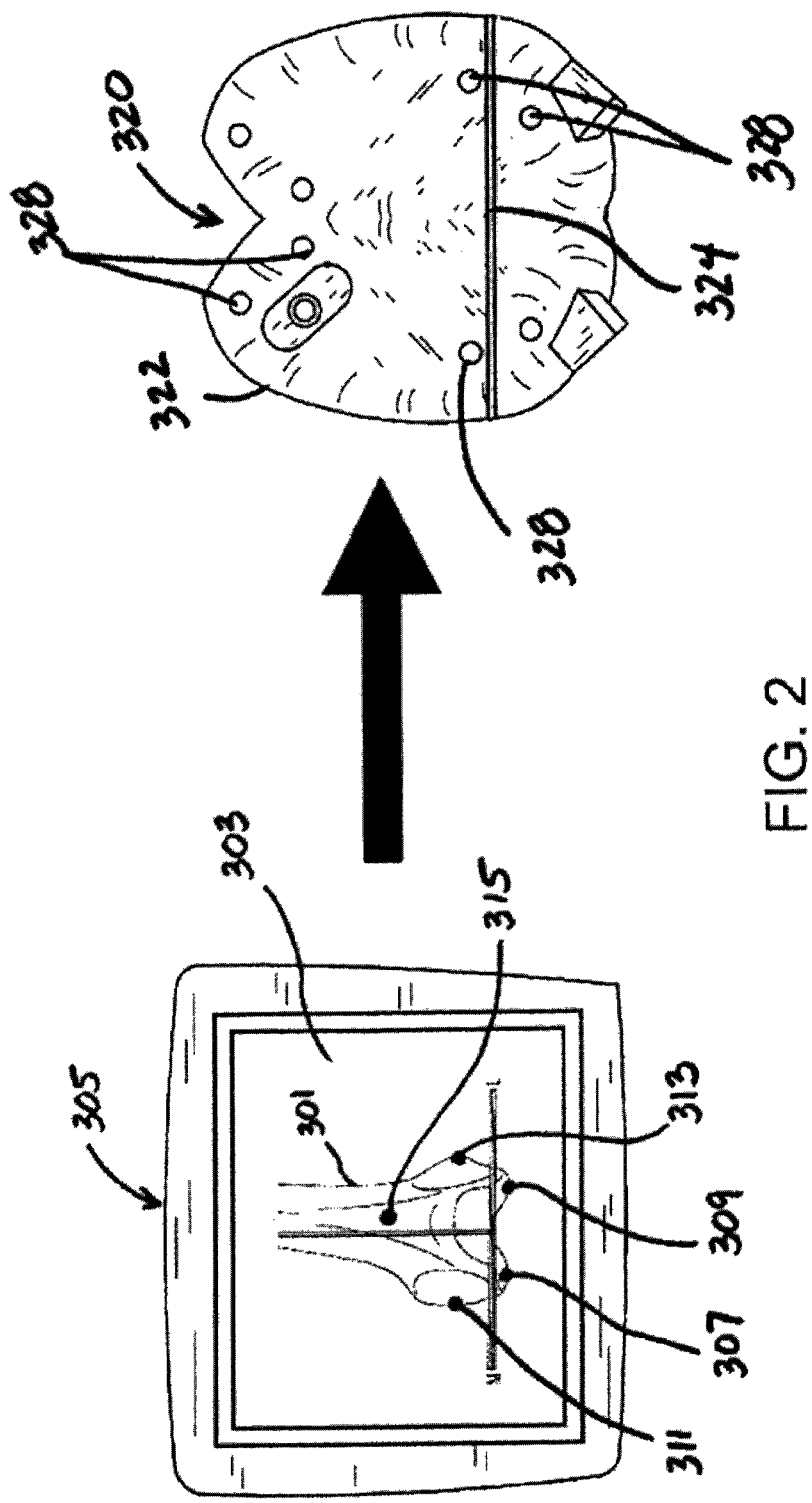
FIG. 2 is a patient-matched surgical component created from a preoperative scan image of the patient's bone.

The principles upon which exemplary embodiments of the present invention rely can be understood with reference to FIG. 2, which illustrates three-dimensional bone model 301 on surgical display image or user interface screen 303 of monitor 305. Model 301 is based on an image of the patient's anatomy, which was obtained from a preoperative diagnostic imaging procedure, such as by magnetic resonance imaging (MRI), computer assisted tomography (CT), fluoroscopy, ultrasound or positron emission tomography (PET). It should be understood that model 301 is intended to illustrate general principles of the present teachings and is not representative of any particular screen shot that a surgeon may observe during a surgical navigation procedure. Moreover, it should be understood and appreciated herein that processes for generating three-dimensional models from preoperative images of anatomical features are well known by those within the surgical navigation field and therefore not discussed in detail herein.

Once three-dimensional model 301 has been created, it is then used by the software program to identify and locate specific known anatomical landmarks characteristic of the anatomical feature. The number of anatomical landmarks identified on the model will depend on the bony anatomy that is being characterized, as well as what type of surgical procedure is being performed on the patient undergoing the operation. In some exemplary embodiments, however, less than about ten anatomical landmarks are identified by the software program and represented on the three-dimensional model. In other exemplary embodiments, less than about seven anatomical landmarks are identified, while in still other exemplary embodiments, less than about three landmarks are identified.

In FIG. 2, model 301 depicts five bony anatomical landmarks common to a typical femur. These bony landmarks include the distal most point of the medial femoral condyle 307, the distal most point of the lateral femoral condyle 309, the medial epicondyle 311, the lateral epicondyle 313 and the anterior cortex point of the femur 315. By acquiring such bony landmarks, the surgeon can use such information to assist in planning the surgical protocol to be performed on the patient. For instance, by acquiring the epicondyles (311, 313), the transepicondylar axis of the femur can be determined to assist with the rotation and positioning of a femoral implant component. Moreover, by acquiring the anterior cortex point of the femur 315, proper implant sizing techniques can be utilized.

Once model 301 has been created and the bony anatomical landmarks identified, the surgeon can use the model as a visual aid and manipulate it to gather important surgical information, such as gap analysis data, resection plane details and bone alignment angles. Furthermore, if the surgeon desires, he can rotate or manipulate model 301 so that he can visually appreciate the general shape and characteristics of the patient's femur, particularly as the acquired bony anatomical landmark points shown on the model remain accurate as it is manipulated by the surgeon. In addition to displaying the acquired femoral landmark points (i.e. points 307, 309, 311, 313 and 315), model 301 can also depict a representation of the implant component that will be implanted onto the patient during the surgical procedure. By displaying a representation of the implant on the bone model, the system can gather additional information useful for finalizing the surgical protocol, particularly implant sizing and rotation information. The representation of the implant can also be rotated and aligned preoperatively, particularly so that the navigation system can calculate the location of necessary bone cuts and/or resection planes to be used during the surgical procedure. Some resection planes that can be determined preoperatively include, but are not limited to, the tibial proximal cut, the femoral distal cut, the femoral anterior cut, as well as the chamfer cuts made by a 4-in-1 resection block.

After the surgical protocol has been planned and is approved, the software then creates a virtual surgical component that is custom-shaped to effect implementation of the surgical specifications (e.g., bone cuts, resection planes, drill holes, etc.) that were determined by the planning software. In some exemplary embodiments, the surgical component may function as a patient-matched reference array and not include any cut slots in its body design. More particularly, in certain embodiments, the surgical component may replace one or more rigid bone reference arrays or markers typically attached to the patient's anatomy during a surgical procedure. By eliminating the use of such rigid bone reference arrays, the surgical procedure can be performed in a minimally invasive manner, particularly as fewer incisions would be required of the patient's anatomy. Reducing the number of required incisions during a surgical procedure is advantageous, particularly in terms of reducing associated scarring and/or complications typically caused from such incisions.

Figure 3A:
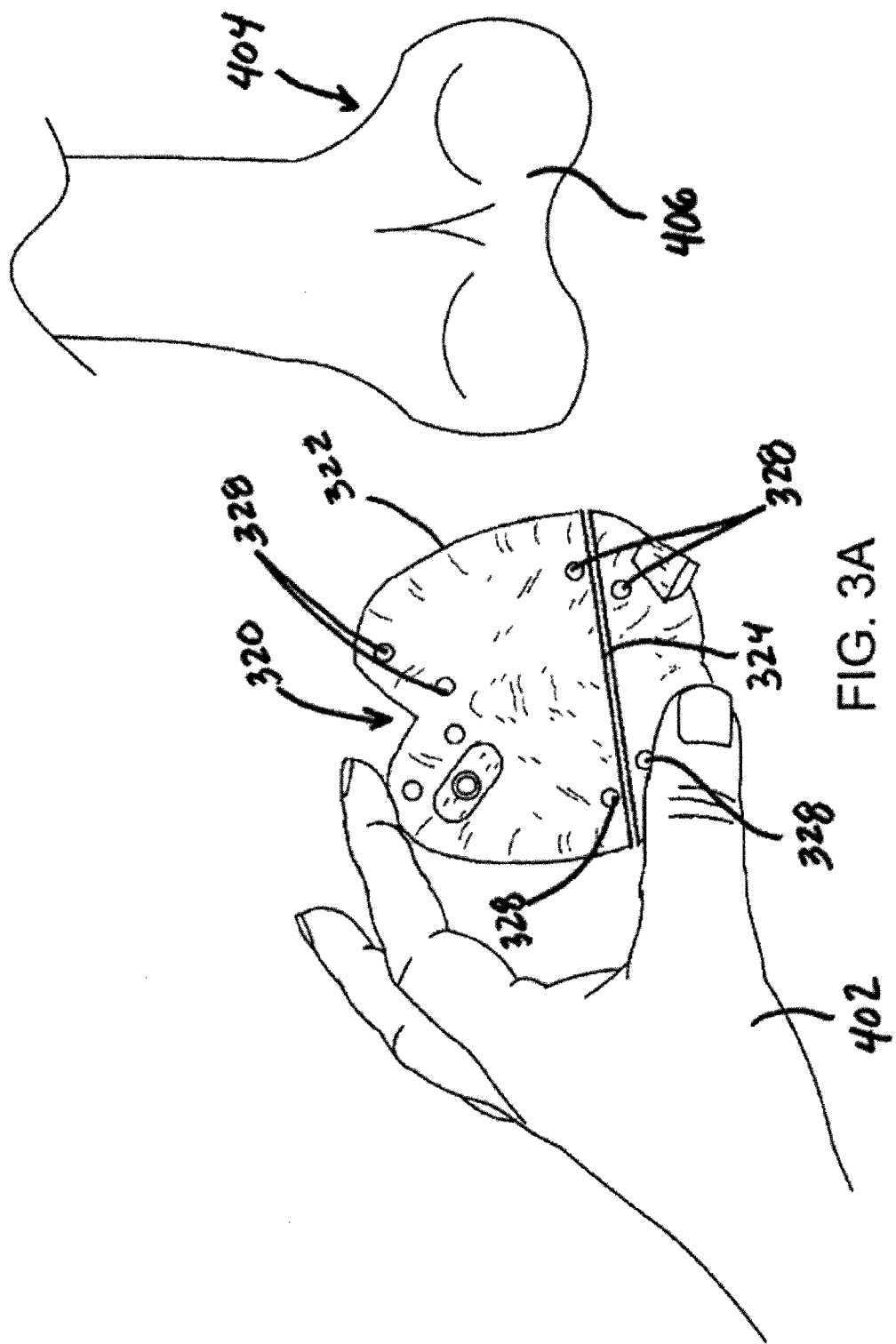
FIG. 3A is a fragmentary perspective view of a surgeon aligning the patient-matched surgical component of FIG. 2 with a bone.
Figure 3B:
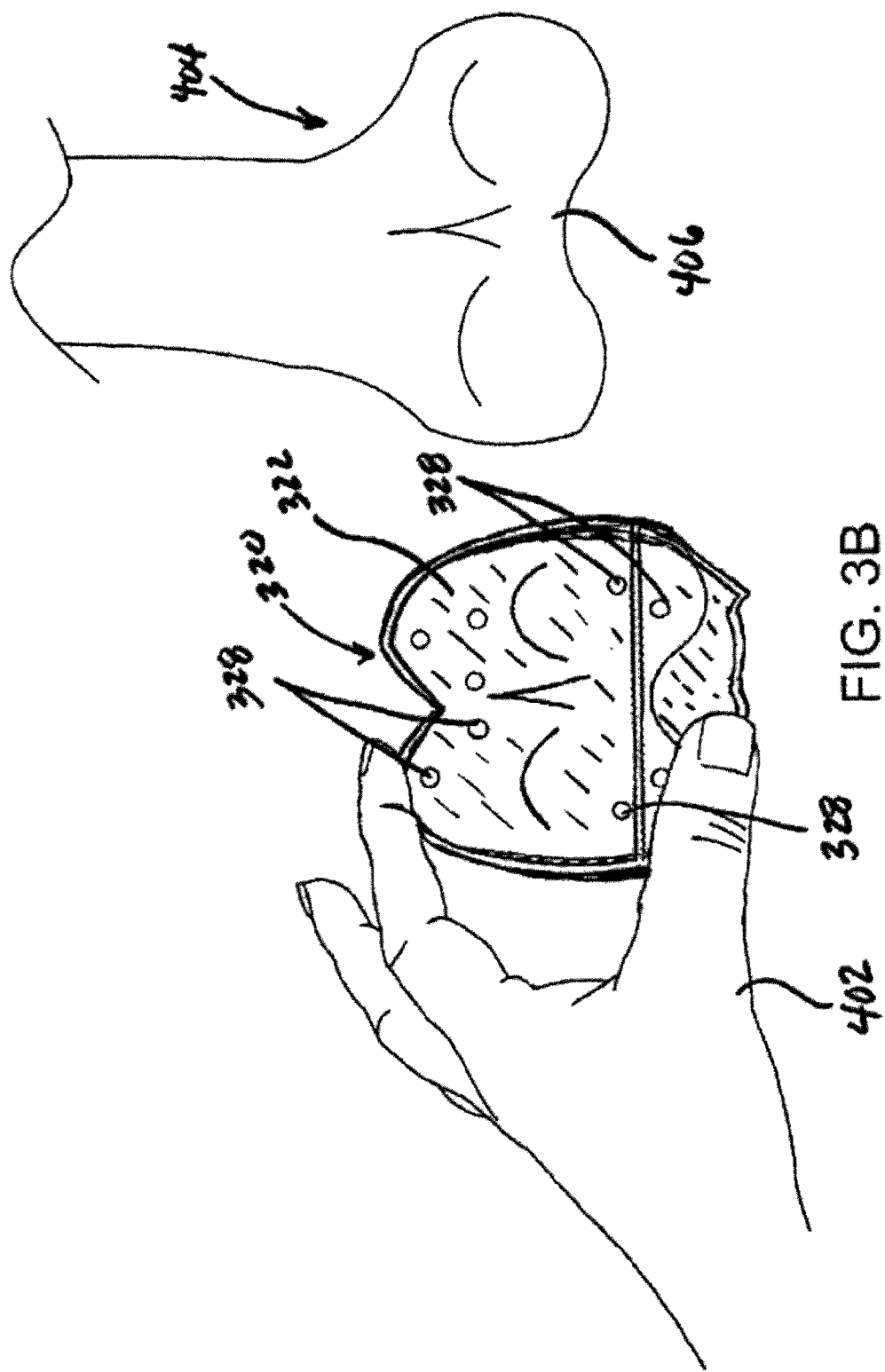
FIG. 3B is a fragmentary perspective view of the backside of the surgical component of FIG. 3A, the component being shown aligned with a bone.

Once the component has been virtually designed, the virtual representation is then sent to a rapid prototyping machine or a standard machining process, which in turn manufactures a physical component that corresponds to the dimensional parameters of the virtual component. For instance, as shown in FIGS. 2, 3A and 3B, surgical component 320 has been created having an interior surface 322, which matches the topography of model 301. Surgical component 320 also includes one or more cutting slots or guides 324, which are specifically designed to accommodate cutting devices (e.g., saw blades) during a bone resection process. It should be understood and appreciated herein that the position, shape and directional orientation of the cutting slot(s) on the surgical component will depend particularly on the surgical procedure that is to be performed on the given patient. For instance, if the surgeon will be performing a total knee arthroplasty, a cutting slot to accommodate the distal femur cut, such as slot 324 shown in FIG. 2, may be included. Surgical component 320 may also include one or more holes 328 to accommodate drilling into the patient's bone and/or attaching the component to the patient's bone during a surgical procedure.

FIGS. 3A and 3B show surgeon 402 positioning surgical component 320 relative to bone 404 during a surgical procedure. As the interior surface of the surgical component is shaped to substantially match the general topographic landscape and contour of bone 404, the surgeon is able to align the component with the bone in such a manner that the component mates with the bone in a position predefined by the software. In other words, surgeon 402 is able to press inner surface 322 of surgical component 320 against outer surface 406 of bone 404 until a tactile sensation is felt by the surgeon indicating that the component has mated with or "matched" its corresponding surface of the bone. Because surgical component 320 is patient-matched to the shape of bone 404, surgeon 402 can position surgical component 320 by feel with a high degree of precision. More particularly, the body of the surgical component is shaped in such a manner that it interfits or interlocks to the shape of the anatomical feature during installation. This interfitting or interlocking relationship allows the surgeon to achieve the tactile sensation when the surgical component is correctly installed onto the anatomical feature. When the surgical component 320 is properly or correctly installed, it sits substantially flush against the surface of bone 404, i.e., there will not be significant gaps around the edge of the component as it sits against the patient's anatomical feature or bone.

As explained above, surgical component 320 further includes one or more holes 328 for drilling into the bone and/or for attaching the component to the bone's surface during a surgical procedure, as well as one or more cutting slots 324 to accommodate cutting devices during a bone resection process. According to one exemplary embodiment, holes 328 are configured to function as anchoring holes, which can be used for inserting temporary pins or screws into the bone to hold the surgical component into place during a surgical procedure. Holes 328 may also be configured into various dimensional patterns and arrangements to accommodate the surgical plan and/or to accommodate the anatomical shape of the bony structure or anatomical feature to which the component is to be affixed. Moreover, in certain exemplary embodiments, the same surgical component may be used in multiple resection procedures, whereby the holes are arranged such that the remaining portion of surgical component 320 remains securely fastened to the bone after the initial resection is completed. Holes 328 may also be configured to use previously placed reference markers or anchors already attached to the surface of the bone. More particularly, according to this embodiment, the arrangement of the holes can be positioned such that the surgeon places the surgical component over one or more reference markers or anchor devices previously placed into the bone. Such reference markers or anchor devices may have been placed during prior diagnostic or therapeutic surgeries, or may have been placed preoperatively for use in future diagnostic or therapeutic procedures.

Figure 4:
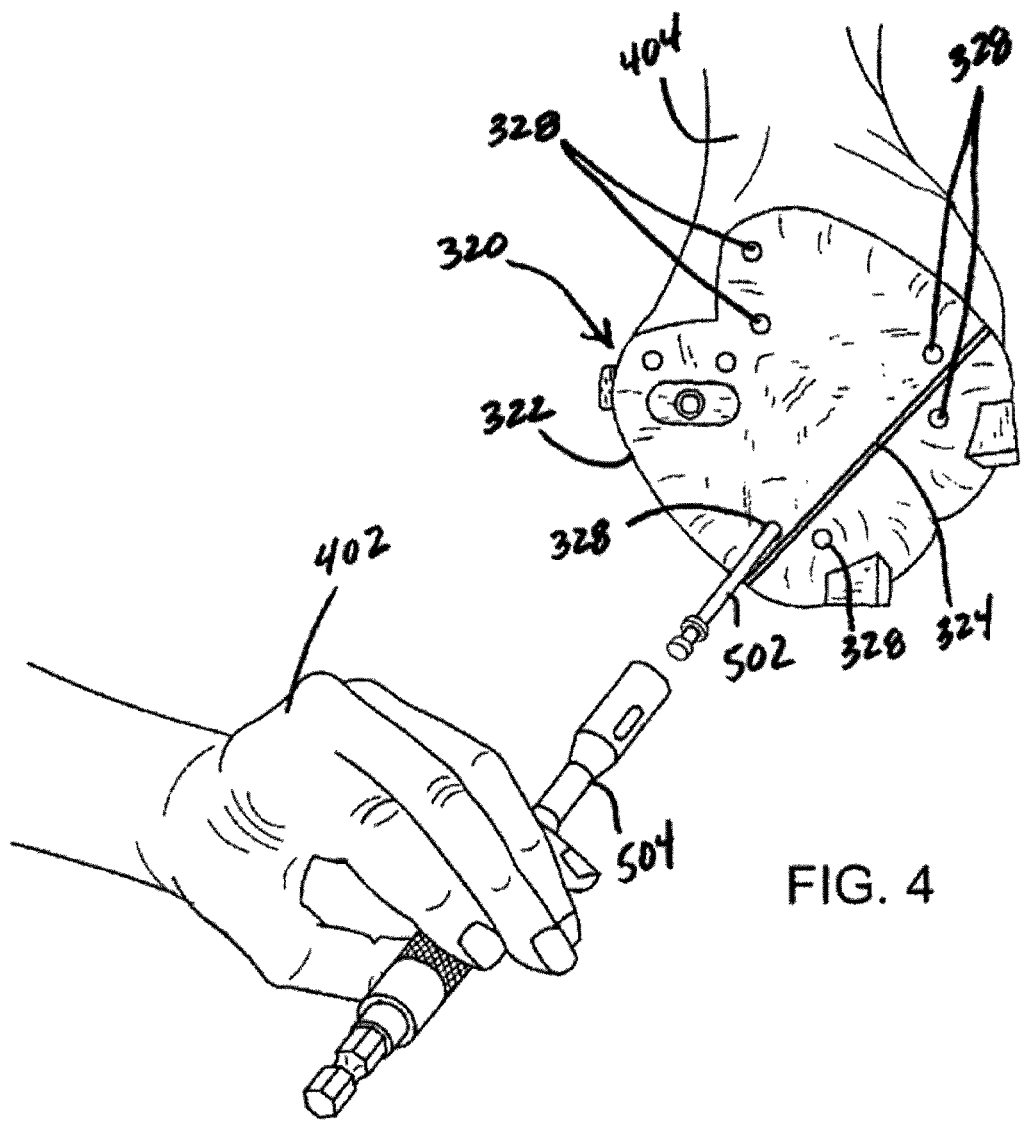
FIG. 4 is a fragmentary perspective view of the patient-matched surgical component of FIG. 2 being attached to the bone by the surgeon.

FIG. 4 shows surgical component 320 aligned with and positioned substantially flush against bone 404. Once positioned, surgical component 320 can be affixed to bone 404 by inserting one or more pins 502 into the bone through holes 328. Affixing surgical component 320 to bone 404 with pins, screws, or other attachment means insures that the surgical component is securely held in place during the surgical procedure. In FIG. 4, surgeon 402 is shown using a pin insertion device 504 to insert pin 502 into bone 404 through one of holes 328. Such surgical pin insertion techniques and instrumentation are known by those of skill within the art and therefore not discussed in detail herein.

Figure 5:
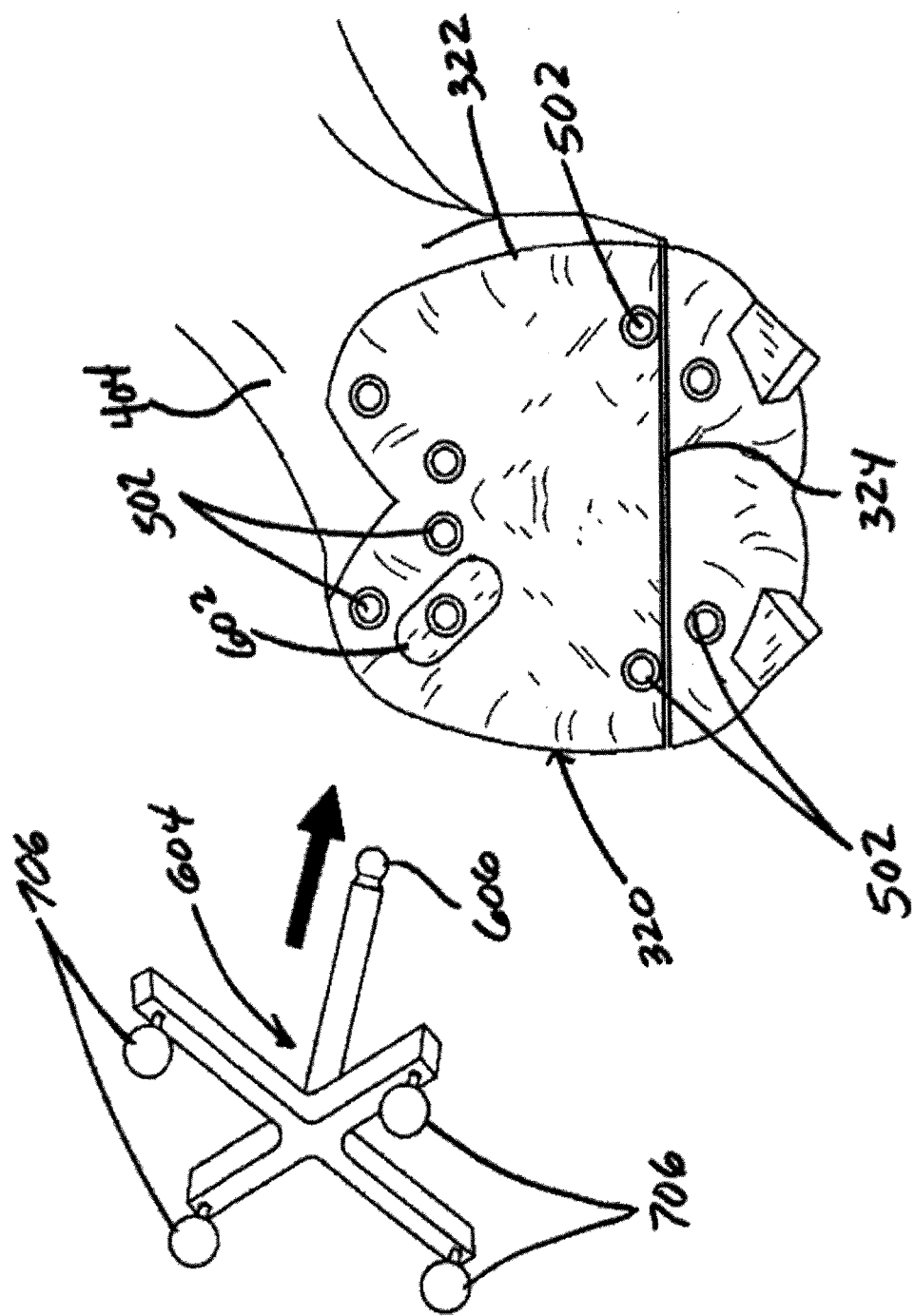
FIG. 5 is a fragmentary perspective view of the patient-matched surgical component of FIG. 4 attached to the bone and its corresponding reference array, which is connectable thereto.

FIG. 5 shows surgical component 320 positioned against bone 404 and secured into place with attachment pins 502. Surgical component 320 also includes a quick connect receptacle 602, which is configured to connect to a tracking device, such as a reference array. According to this embodiment, tracking or reference array 604 is provided with a quick connect base 606 that dimensionally corresponds with receptacle 602 such that a removable snap-fit connection can be achieved between the two components. While FIG. 5 illustrates a snap-fit attachment means between the reference array and the component, it should be understood that in other embodiments, reference array 604 may be "pre-installed" onto surgical component. 320, whereby no additional attachment means is required after the component is attached to the bone. It should also be understood and appreciated that any attachment means known within the art may be used to secure reference array 604 to surgical component 320. Such attachment means include, but are not limited to, welding, fusing, molding, gluing, threading, snap-connections, quick disconnect connections and the like.

Once reference array 604 is attached to surgical component 320, navigation system 20 is able to locate and track its position in real-time and display its tracked position on a surgical plan image. In other words, once the navigation system locates the array, the system automatically knows its position with respect to the landmarks identified on the model image, as well as where it has been pre-registered with respect to the image. To accomplish this, and with reference to FIG. 6, cameras 702 of optical locator 704 detect in space the position of markers 706, which extend from the surface of reference array 604. It should be understood and appreciated herein that while this embodiment shows four markers 706 attached to the frame of reference array 604, in other embodiments less than four markers may be used, while in yet other embodiments, more than four markers may be used. For instance, in some embodiments using electromagnetic tracking technology, only one marker is needed to track the position of the surgical component in space. In yet other embodiments, three markers may be used to triangulate the position of the surgical component in space. As such, it should be fully appreciated that the present teachings are not intended to be limited herein.

To detect the position of the markers in space, known triangulation methods are used. These triangulation methods allow the navigation system to determine the relative location of the reference array and its markers with respect to the patient's anatomy, and then display the same on a surgical plan image. As reference array 604 is trackable in real-time, the position of bone 404 can also be tracked in real-time, particularly since reference array 604 is fixably attached to its surface by way of surgical component 320. As explained above, by having reference array 604 positioned relative to the surgical component 320 in a predefined spatial manner, the need for intra-operative registration during the surgical procedure is substantially minimized.

As used herein, "predefined" refers to a preoperatively planned spatial relationship between the surgical component and the anatomical feature of the patient to which the component is to be attached. In other words, once the component is installed onto the anatomical feature in its predefined spatial orientation, it is automatically registered with the system and can be tracked by the navigation system for the remainder of the procedure without further registration techniques. Moreover, since the patient matched component is fixably secured to the patient's anatomy throughout the surgical procedure, reference array 604 is able to function as a rigid reference bone marker to track bone 404 during the surgical procedure. Such rigid bone reference arrays are commonly used in orthopaedic surgical procedures and are able to track a patient's bones with respect to various surgical instruments during a surgical navigation procedure. Because the presently disclosed reference arrays are preoperatively registered with the navigation system in a predefined manner with respect to the patient's anatomy, these components can be used to track the patient's anatomy without the need to insert additional rigid array markers into the patient during the procedure. Moreover, because such surgical components are registered with the navigation system during the preoperative planning steps of the surgical procedure, timely intraoperative registration processes are also unnecessary.

Figure 6:
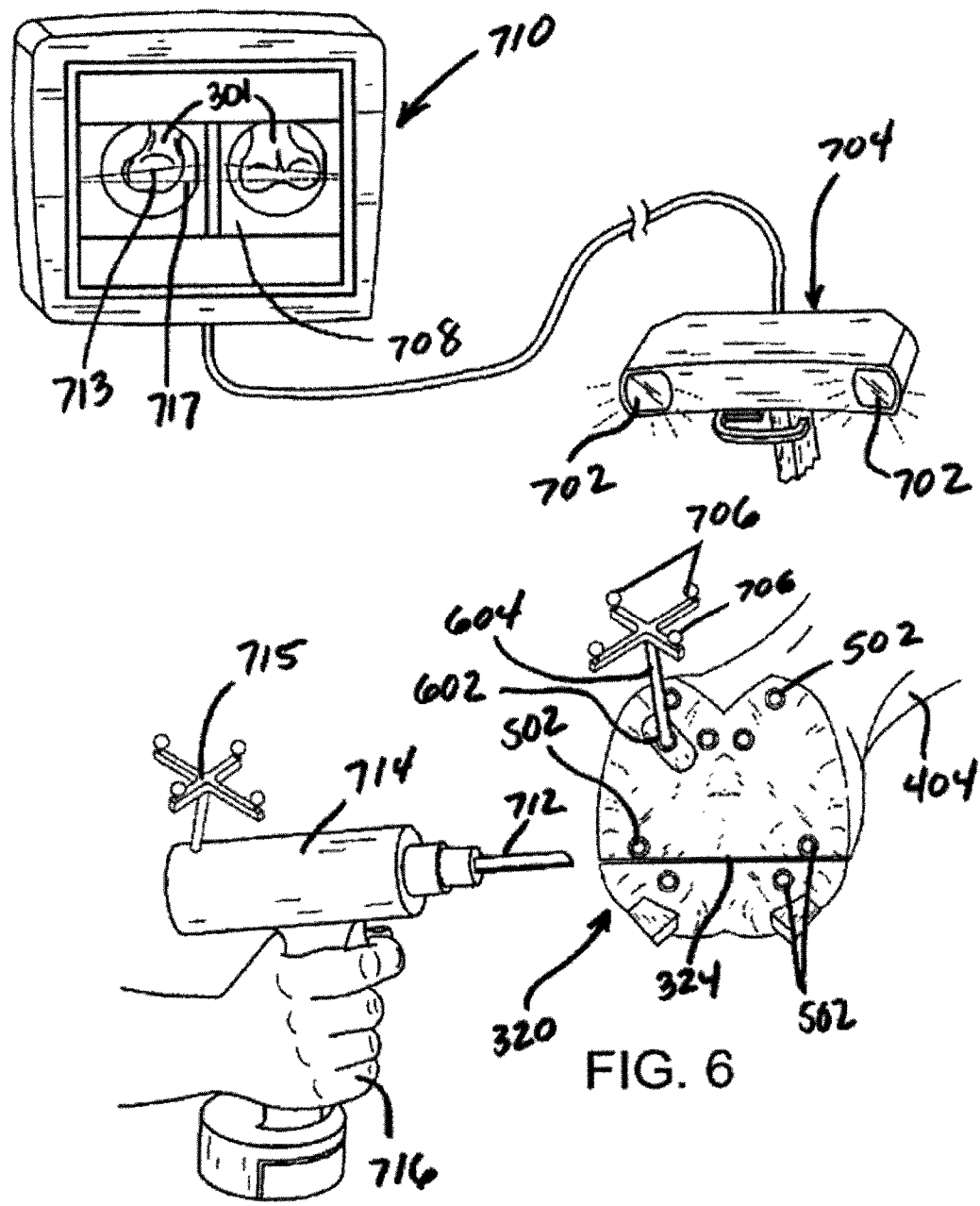
FIGS. 6 and 7 are fragmentary perspective views illustrating the bone of FIG. 5 undergoing an exemplary resection process in accordance with the present teachings.
Figure 7:
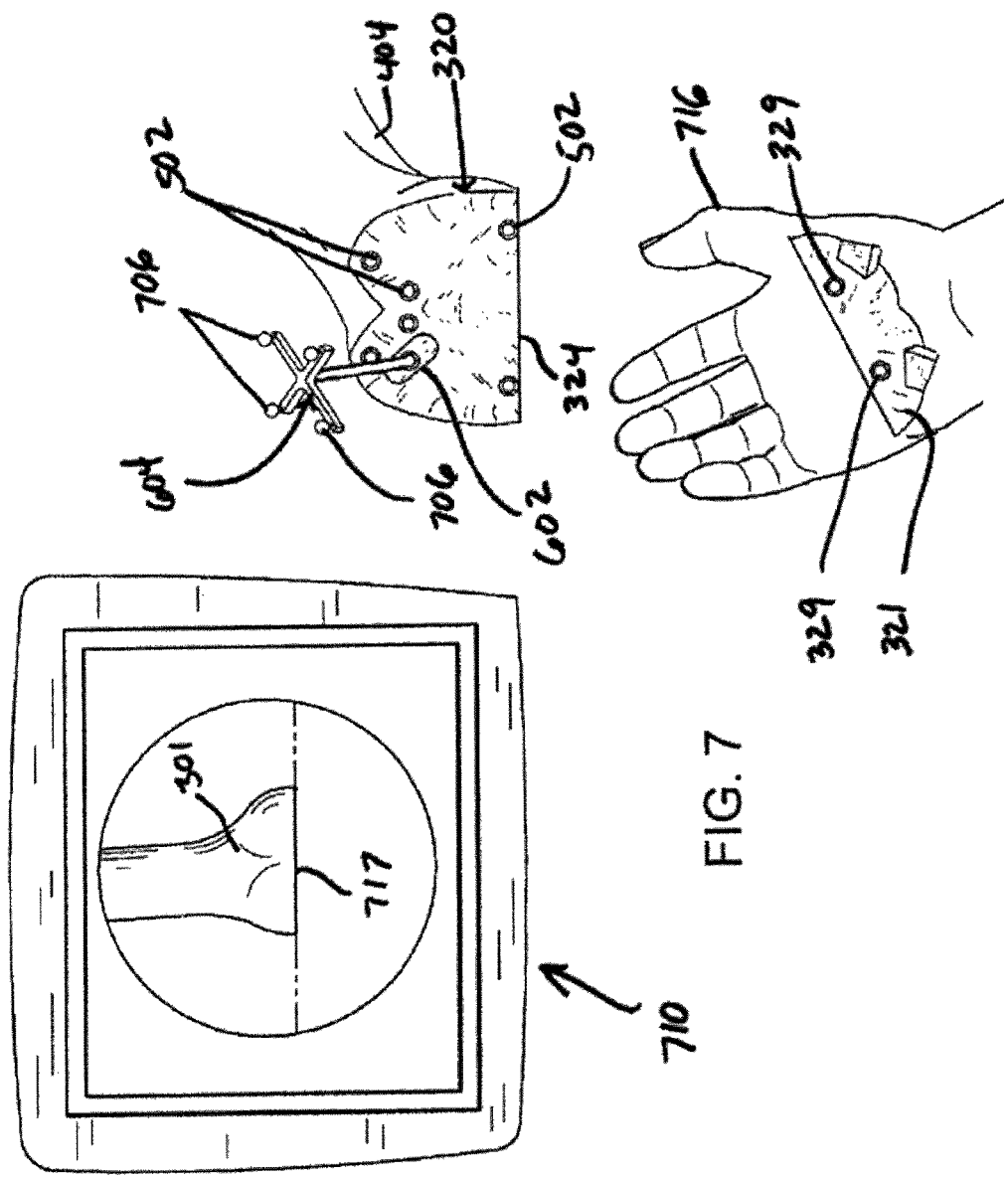

An exemplary illustration of a bone undergoing a resection process in accordance with the present teachings is depicted in FIGS. 6-7. Surgical instrument 714 may optionally include a marker array 715, which can be further identified and tracked by cameras 702 of optical locator 704. However, since surgical component 320 was custom designed to match and mate with the specific shape of bone 404, the surgeon does not need to track the position of the surgical instrument relative to the bone during the surgical procedure. More particularly, the position of cutting slot 324 on surgical component 320 was previously registered with the tracking system during the preoperative planning stages of the surgical procedure. As such, once the surgeon attaches the component to the bone in its predetermined position, he can proceed directly to resecting the bone with the surgical instrument without further tracking or registering of the surgical instrument. As such, it should be understood that the depiction of marker array 715 on surgical instrument 714 is optional and is not intended to limit the scope of the present teachings.

Referring still to FIGS. 6 and 7, as surgeon 716 moves instrument 714 relative to bone 404, the tracking system locates and tracks marker array 715 in real-time. The relative location of marker array 715 is then shown on surgical plan image 708 of computer display 710. The tracking system detects the location of surgical instrument 714 relative to bone 404 by referencing the position of marker array 715 as it moves with respect to reference array 604, which is fixably attached to bone 404 by way of surgical component 320. The position of saw blade 712 of surgical instrument 714 is displayed on surgical plan image 708 as cut plane 713. By viewing cut plane 713 on surgical plan image 708, surgeon 716 can confirm that the surgical component is positioned properly, although as just noted, this step is optional since the component can be properly positioned by the surgeon by feel alone.

FIG. 7 shows a portion of bone 404 removed after surgeon 716 has inserted saw blade 712 into cut slot 324 of surgical component 320. A portion of the surgical component 321 remains affixed to the removed bone by attachment pin 329. Because reference array 604 is still attached to bone 404 by way of surgical component 320, the surgical navigation system continues to recognize and track the position of bone 404 and the remaining portion of the attached surgical component 320 in real-time throughout the remainder of the surgical procedure. As such, the remaining portion of surgical component 320, and its reference array 604, can be used for additional steps in the surgical procedure, such as the removal or modification of a second predefined part of the bone after the initial resection, or the placement and use of additional surgical components. The tracked remaining portion of surgical component 320 can also be used to perform other surgical procedures that require tracking, such as ligament balancing, range of motion and impingement analyses.

It should be understood and appreciated herein that while FIG. 7 depicts portion 321 of surgical component 320 being removed with saw blade 712, in other exemplary embodiments, portion 321 may be removed by being snapped, broken or cleaved away from surgical component 320. For instance, cut slot 324 could be replaced by a groove or cleave that is designed to be physically broken or torn away from the surgical component after it has been attached to the patient's anatomy. As such, the attachment means useful for the present teachings are not intended to be limited herein.

While the above-described embodiments illustrate the presently disclosed surgical components as being useful for knee related applications, it should be appreciated and understood herein that the exemplary components disclosed herein may also be used together with any other anatomical features without straying from the present teachings. For instance, in certain exemplary embodiments, the surgical components may also be used together with hip-related navigation applications. More particularly, as is known within the surgical navigation field, registration processes for the hip can be quite challenging, particularly as the surgeon must register both sides of the patient's pelvis, including rolling the patient onto their side to collect data points and then re-draping and re-scrubbing the patient between such registration steps. By using the presently disclosed surgical components, navigating the hip during a surgical procedure is significantly simplified, particularly as the need to register the hip intraoperatively is eliminated.

Figure 8:
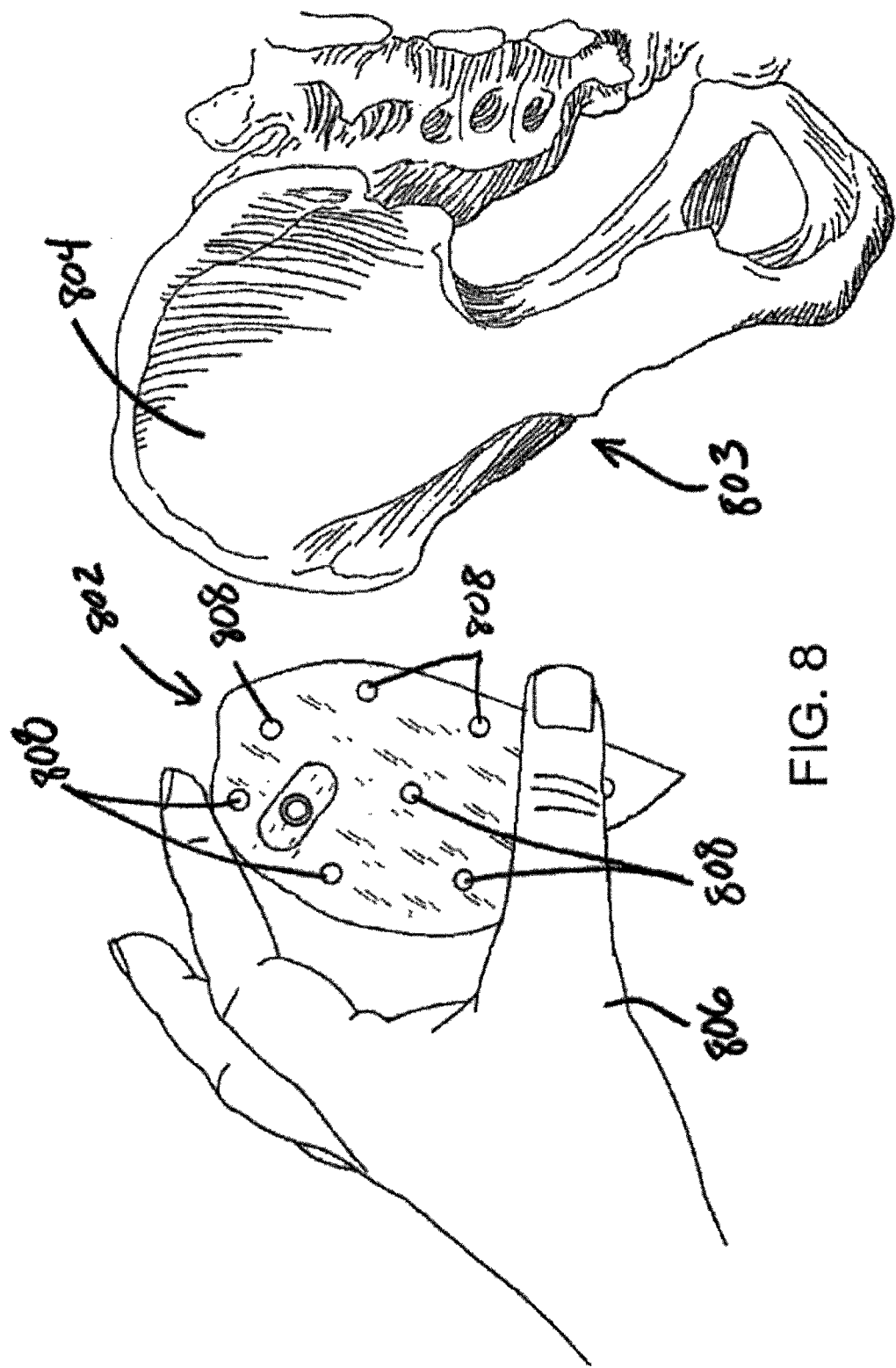
FIG. 8 is a fragmentary perspective view of a surgeon aligning a patient-matched surgical component with a patient's pelvis in accordance with the present teachings.

Further principles upon which exemplary embodiments of the present invention rely can be understood with reference to FIG. 8. FIG. 8 depicts surgical component 802, which has been created by a rapid prototyping machine or a standard machining process to match the dimensional parameters of a virtual representation of a patient's pelvis according to the process described above. More particularly, surgical component 802 has an interior surface that matches the topographic landscape of pelvis 803. According to this embodiment, surgeon 806 positions surgical component 802 relative to pelvis 803 during a hip procedure. As the interior surface of the surgical component is shaped to substantially match the general topographic landscape and contour of pelvis 803, the surgeon is able to align the component with the pelvis in such a manner that the component mates with the pelvis in a position predefined by the software. In other words, surgeon 806 is able to press the inner surface of surgical component 802 against outer surface 804 of pelvis 803 until a tactile sensation is felt by the surgeon indicating that the component has mated with or "matched" its corresponding surface of the pelvis. Because surgical component 802 is patient-matched to the shape of pelvis 803, surgeon 806 can position surgical component 802 by feel with a high degree of precision. When properly positioned, surgical component 802 will sit substantially flush against the surface of pelvis 803, i.e., there will not be significant gaps around the edge of the component as it sits against the patient's pelvic bone.

Figure 9:
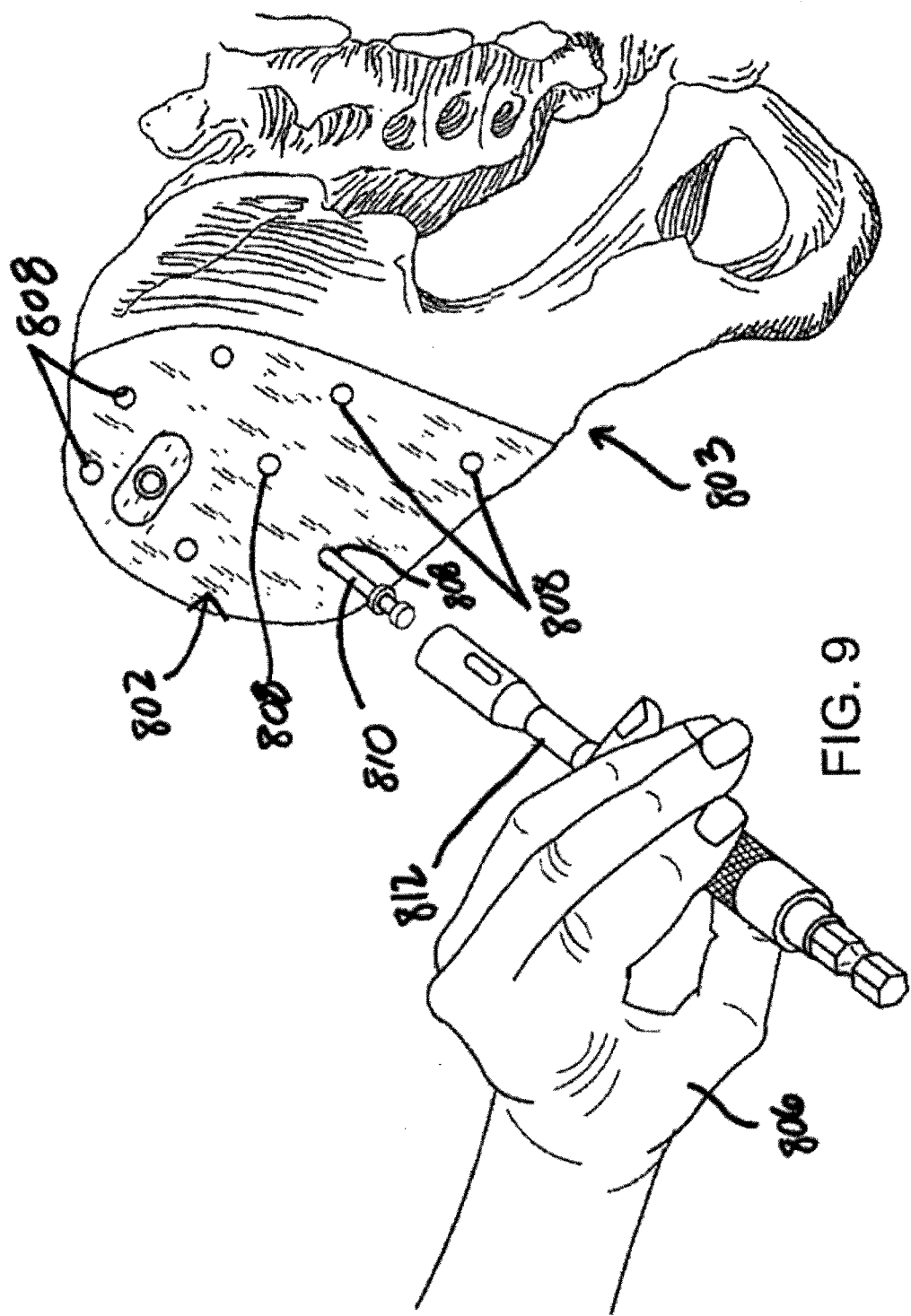
FIG. 9 is a fragmentary perspective view of the patient-matched surgical component of FIG. 8 being attached to the pelvis by the surgeon.

Surgical component 802 also includes one or more holes 808 for drilling into the pelvis and/or for attaching the component to the pelvis's surface during a hip procedure. According to one exemplary embodiment, holes 808 are configured to function as anchoring holes, which can be used for inserting temporary pins or screws into the pelvis, thereby holding the surgical component into place during a surgical procedure. For instance, FIG. 9 shows surgical component 802 aligned with and positioned substantially flush against pelvis 803. Once positioned, surgical component 802 can be affixed to pelvis 803 by inserting one or more pins 810 into the pelvis through holes 808. Affixing surgical component 802 to pelvis 803 with pins, screws, or other attachment means insures that the surgical component is securely held in place during the surgical procedure. In FIG. 9, surgeon 806 is shown using a pin insertion device 812 to insert pin 810 into pelvis 803 through one of holes 808.

Figure 10:
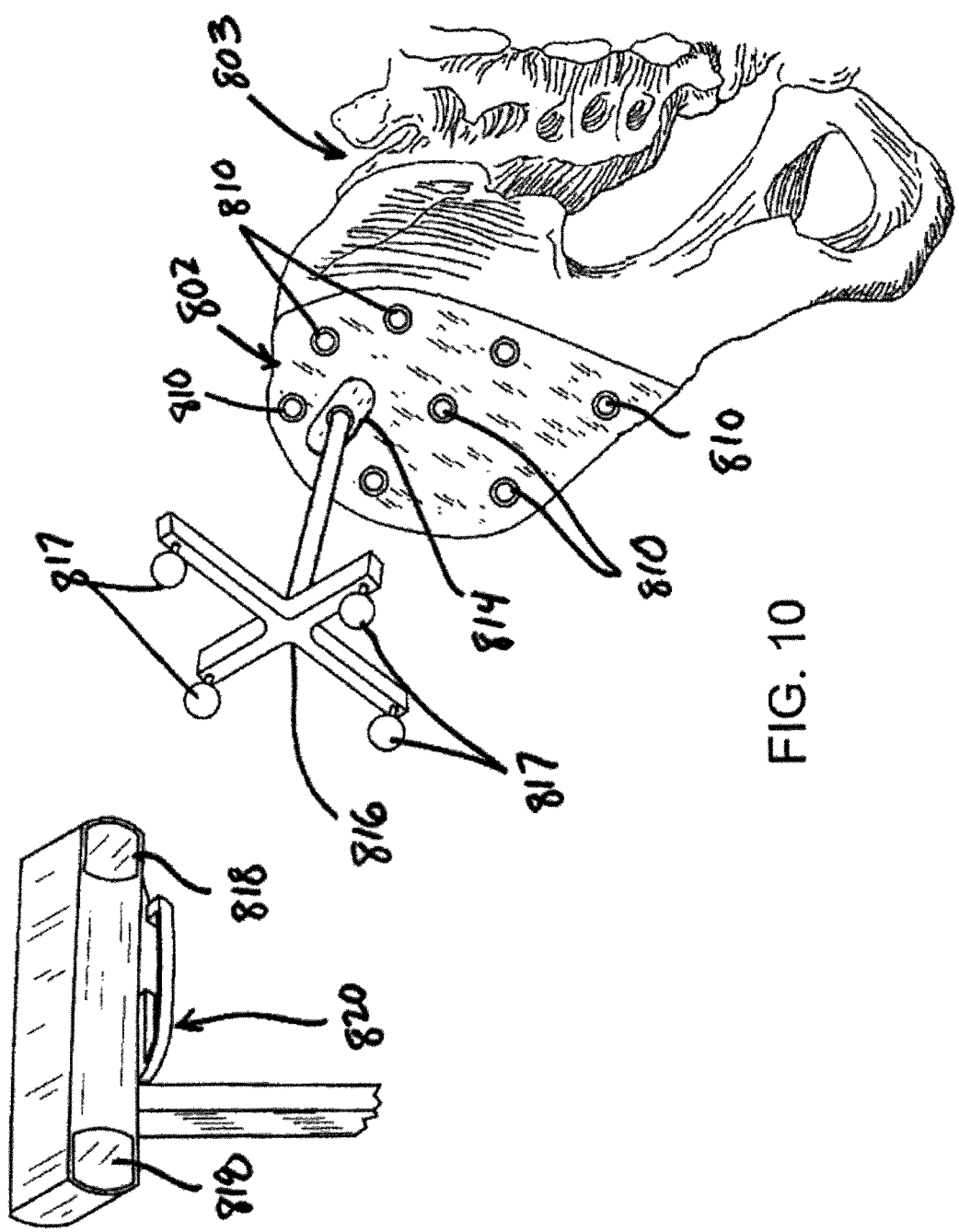
FIG. 10 is a fragmentary perspective view of the patient-matched surgical component of FIG. 8 and its corresponding reference array connected thereto.

FIG. 10 shows surgical component 802 positioned against pelvis 803 and secured into place with attachment pins 810. Surgical component 802 also includes a quick connect receptacle 814, which is configured to connect to a tracking device, such as reference array 816. Once reference array 816 is attached to surgical component 802, navigation system 20 is able to locate and track its position in real-time and display its tracked position on a surgical plan image. In other words, once the navigation system locates the array, the system automatically knows its position with respect to the landmarks identified on the model image, as well as where it has been pre-registered with respect to the image. To accomplish this, cameras 818 of optical locator 820 detect in space the position of markers 817, which extend from the surface of reference array 816. To detect the position of the markers in space, known triangulation methods are used. These triangulation methods allow the navigation system to determine the relative location of the reference array and its markers with respect to the patient's anatomy, and then display the same on a surgical plan image. As reference array 816 is trackable in real-time, the position of pelvis 803 can also be tracked in real-time, particularly since reference array 816 is fixably attached to its surface by way of surgical component 802. As explained above, by having reference array 816 positioned relative to the surgical component 802 in a predefined spatial manner, the need for intra-operative registration during the surgical procedure is substantially minimized.

In additional to navigating knees and hips, the present teachings can also be used with surgical procedures involving the shoulder, spine, ankle, elbow, skull or any other type of bony structure found within the human anatomy. As such, the present teachings are not intended to be limited herein.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of automatically registering a surgical navigation system to a patient's anatomy, comprising:
using the surgical navigation system to pre-register a first spatial relationship between a surgical component and a reference array connected to the surgical component;
using the surgical navigation system to pre-register a second spatial relationship between an anatomical feature of a patient and the surgical component;
installing the surgical component on the patient such that the surgical component engages the anatomical feature in the second spatial relationship; and
locating the reference array with the surgical navigation system to automatically register the position of the reference array relative to the patient's anatomy wherein the navigation system automatically registers the position of the reference array relative to the patient's anatomy when the reference array is within a measurement field of the navigation system.

2. The method of claim 1, wherein installing the surgical component onto the patient comprises mating a surface of the surgical component with a corresponding surface on the anatomical feature, the corresponding surface on the anatomical feature being shaped to substantially correspond to the shape of the surgical component's surface.

3. The method of claim 2, wherein installing the surgical component on the patient comprises adjusting the position of the surgical component relative to the anatomical feature until a tactile sensation of correct placement is achieved.

4. The method of claim 2, wherein mating the surface of the surgical component with the corresponding surface on the anatomical feature comprises attaching the surgical component to the anatomical feature with at least one of pins and screws.

5. The method of claim 1, further comprising identifying a finite number of predefined points on a representative model of the anatomical feature, the model being generated from a preoperative image of the patient's anatomy.

6. The method of claim 5, wherein at least one of the predefined points is a bony anatomical landmark selected from at least one of a femoral head landmark, a central knee landmark, a medial femoral condyle landmark, a lateral femoral condyle landmark, a medial epicondyle landmark, a lateral epicondyle landmark, a medial posterior condyle landmark, a lateral posterior condyle landmark and an anterior cortex point landmark.

7. The method of claim 5, further comprising using the surgical navigation system to calculate a bone cut by analyzing the predefined points on the model.

8. The method of claim 1, further comprising removing a portion of the anatomical feature and a portion of the installed surgical component.

9. The method of claim 8, further comprising tracking a remaining portion of the anatomical feature with the surgical navigation system, the remaining portion of the anatomical feature including a portion of the installed surgical component, the remaining portion of the installed surgical component including the reference array.

10. The method of claim 1, wherein the navigation system automatically registers the position of the reference array relative to the patient's anatomy when the surgical component is attached to the anatomical feature of the patient.

11. The method of claim 1, further comprising using the surgical navigation system to simultaneously track movement of the anatomical feature and the surgical component with the reference array while the surgical component is installed on the patient and moved within a measurement field of the tracking system.

12. A method of performing a surgical procedure aided by a surgical navigation system, comprising:
generating a representative model of an anatomical feature from an image of a patient's anatomy;
using the model to make a surgical component, the surgical component having a surface that is shaped to substantially mate with the anatomical feature in a predefined spatial relationship;
installing the surgical component on the anatomical feature by mating the surface of the component with the anatomical feature in the predefined spatial relationship; and
tracking movement of the anatomical feature with a tracking system when the installed surgical component is moved within a measurement field of the tracking system by tracking movement of the surgical component within the measurement field of the tracking system.

13. The method of claim 12, wherein installing the surgical component on the anatomical feature comprises adjusting the position of the surgical component relative to the anatomical feature until a tactile sensation of correct placement is achieved.

14. The method of claim 12, wherein tracking movement of the anatomical feature with the tracking system comprises tracking movement of a reference array attached to the surgical component.

15. The method of claim 12, further comprising identifying a finite number of predefined points on the anatomical feature, the predefined points being shown on the model to assist in making the surgical component.

16. The method of claim 15, wherein at least one of the predefined points is a bony anatomical landmark selected from at least one of a femoral head landmark, a central knee landmark, a medial femoral condyle landmark, a lateral femoral condyle landmark, a medial epicondyle landmark, a lateral epicondyle landmark, a medial posterior condyle landmark, a lateral posterior condyle landmark and an anterior cortex point landmark.

17. The method of claim 12, further comprising removing a portion of the anatomical feature and a portion of the installed surgical component.

18. The method of claim 17, further comprising tracking a remaining portion of the anatomical feature with the surgical navigation system, the remaining portion of the anatomical feature including a portion of the installed surgical component, the remaining portion of the installed surgical component including the reference array.

19. A method of performing a surgical procedure aided by a surgical navigation system, comprising:
generating a representative model of an anatomical feature from an image of a patient's anatomy;
using the model to make a surgical component, the surgical component having a reference array associated therewith and a surface that is shaped to substantially mate with an anatomical feature in a predefined spatial relationship;
installing the surgical component on the anatomical feature by mating the surface of the component with the anatomical feature in the predefined spatial relationship;
tracking movement of the anatomical feature with the tracking system when the installed surgical component is moved within a measurement field of the tracking system;
removing a portion of the anatomical feature, the removed portion also including a portion of the installed surgical component; and
tracking a remaining portion of the anatomical feature with the tracking system, the remaining portion of the anatomical feature including a portion of the installed surgical component, the remaining portion of the installed surgical component including the reference array.

20. The method of claim 19, wherein installing the surgical component on the anatomical feature comprises adjusting the position of the surgical component relative to the anatomical feature until a tactile sensation of correct placement is achieved.

21. The method of claim 19, further comprising identifying a finite number of predefined points on the anatomical feature, the predefined points being shown on the model to assist in making the surgical component.

22. The method of claim 21, wherein at least one of the predefined points is a bony anatomical landmark selected from at least one of a femoral head landmark, a central knee landmark, a medial femoral condyle landmark, a lateral femoral condyle landmark, a medial epicondyle landmark, a lateral epicondyle landmark, a medial posterior condyle landmark, a lateral posterior condyle landmark and an anterior cortex point landmark.

23. The method of claim 19, wherein removing a portion of the anatomical feature comprises resecting bone with a saw blade through a cut slot of the surgical component.

24. The method of claim 19, wherein mating the surface of the component with the anatomical feature in the predefined spatial relationship comprises attaching the surgical component to the anatomical feature with at least one of pins and screws.

* * * * *